(12) United States Patent
Archer et al.

(10) Patent No.: US 9,134,301 B2
(45) Date of Patent: Sep. 15, 2015

(54) SORTING OF ADHERENT CELLS BY SELECTIVE TRANSFORMATION OF LABELS

(75) Inventors: Robert M. Archer, Eugene, OR (US); Frank Hsiung, San Francisco, CA (US); Paul Patt, Lafayette, CA (US)

(73) Assignee: Bio-Rad Laboratories, Inc., Hercules, CA (US)

( * ) Notice: Subject to any disclaimer, the term of this patent is extended or adjusted under 35 U.S.C. 154(b) by 0 days.

(21) Appl. No.: 13/298,847

(22) Filed: Nov. 17, 2011

(65) Prior Publication Data

US 2012/0295798 A1 Nov. 22, 2012

Related U.S. Application Data

(60) Provisional application No. 61/416,012, filed on Nov. 22, 2010.

(51) Int. Cl.
*G01N 33/50* (2006.01)
*G01N 15/06* (2006.01)
*G01N 15/14* (2006.01)
*G01N 15/02* (2006.01)

(52) U.S. Cl.
CPC ........ *G01N 33/5094* (2013.01); *G01N 15/0606* (2013.01); *G01N 15/1463* (2013.01); *G01N 2015/0288* (2013.01); *G01N 2015/149* (2013.01)

(58) Field of Classification Search
CPC .......... G01N 33/5094; G01N 15/0606; G01N 15/1463; G01N 2015/149; G01N 2015/0288
USPC ............................................................ 506/7
See application file for complete search history.

(56) References Cited

U.S. PATENT DOCUMENTS

| | | | | |
|---|---|---|---|---|
| 4,965,829 | A * | 10/1990 | Lemelson | 382/101 |
| 7,129,070 | B2 * | 10/2006 | Palsson | 435/173.1 |
| 7,505,618 | B2 | 3/2009 | Palsson et al. | |
| 7,527,940 | B2 * | 5/2009 | Thomas | 435/29 |
| 7,790,406 | B2 | 9/2010 | Cunningham et al. | |
| 7,876,108 | B2 | 1/2011 | Abassi et al. | |
| 2007/0238122 | A1 * | 10/2007 | Allbritton et al. | 435/6 |
| 2007/0238169 | A1 | 10/2007 | Abiliz et al. | |
| 2008/0166378 | A1 | 7/2008 | Schimmer et al. | |
| 2009/0032441 | A1 * | 2/2009 | Corak et al. | 209/3.3 |
| 2009/0112482 | A1 * | 4/2009 | Sandstrom | 702/19 |
| 2009/0212768 | A1 * | 8/2009 | Llandro et al. | 324/228 |
| 2009/0275042 | A1 * | 11/2009 | Emans et al. | 435/6 |
| 2010/0278919 | A1 * | 11/2010 | Denes et al. | 424/489 |
| 2011/0306086 | A1 | 12/2011 | Nitta | |

FOREIGN PATENT DOCUMENTS

WO 2007/118208 A2 10/2007
WO 2010/104014 A1 9/2010

OTHER PUBLICATIONS van de Linde, S., et al. "Photoswitching microscopy with standard fluorophores," Oct. 19, 2008, Applied Physics B, 93, pp. 725-731.*
Keji, Jan F. et al. "High-speed Photodamage Cell Selection Using a Frequency-Doubled Argon Ion Laser," 1995, Cytometry, 19, pp. 209-216.*
Dendramis, Kimberly A. and Daniel T. Chiu, "Laser Photolysis of Dye-Sensitized Nanocapsules Occurs via a Photothermal Pathway," Jun. 17, 2009, JACS, 131, 16771-16778.*
Kobayashi, Tatsuya et al. "Magnetic induction hyperthermia for brain tumor using ferromagnetic implant with low Curie temperature," 1986, Journal of Neuro-Oncology, 4, pp. 175-181.*
"MACS(R) Technology: Gold standard in cell separation," Miltenyi Biotec, Feb. 11, 2007 [Retrieved on Dec. 20, 2012]. Retrieved from the Internet: <www.miltenyibiotec.com/download/.../MACS_Technology_Flyer.pdf>.*
"Demagnetization of Permanent Magnets," Magnetic Component Engineering, Dec. 22, 2007 [Retrieved on Dec. 20, 2012]. Retrieved from the Internet: <www.mceproducts.com/knowledge-base/article/article-dtl.asp?id=90>.*
Davies, Derek. "Cell Sorting by Flow Cytometry" in Macey, Marion G., Flow Cytometry: Principles and Applications (Totowa, NJ; Humana Press Inc.; 2007), pp. 257-276.*
Petracic, O. Feb. 2010 Superlattices and Microstructure 47: 569-578.*
Ondeck, C. L. et al. 2009 Journal of Applied Physics 105, 07B324: 1-3.*
Gunn, et al., "Ferromagnetic Micropallets for Magnetic Capture of Single Adherent Cells," *Langmuir*, vol. 26(22), pp. 17703-17711 (Epub Oct. 22, 2010, Nov. 16, 2010).
Lee, et al., "Light Mediated Spatial Control Via Photolabile Fluorescently Quenched Peptide Cassettes," *J Am Chem Soc.*, vol. 132(5), 8 pages (Feb. 10, 2010).
Maurel, et al., "Photoactivatable and Photoconvertible Fluorescent Probes for Protein Labeling," *ACS Chem Biol.*, vol. 5(5), pp. 507-516 (May 21, 2010).
Patterson, et al., "A Photoactivatable GFP for Selective Photolabeling of Proteins and Cells," *Science*, vol. 297(5588), pp. 1873-1877 (Sep. 13, 2002).

(Continued)

*Primary Examiner* — Christopher M Gross
(74) *Attorney, Agent, or Firm* — Kilpatrick Townsend & Stockton LLP

(57) ABSTRACT

Adherent cells bearing characteristics that are detectable only in the adherent state can be sorted on the basis of these characteristics independently of their adherent state, by applying a transformable label to the entire population of cells, both those bearing the characteristics of interest and those not, in their adherent state and identifying the locations of the cells of interest on the adherent surface. The cells of interest, or all cells other than those of interest, are then selectively treated to transform the labels and achieve differentiation between the cells of interest and the remaining cells. All cells are then released from the adherent state and sorted in the same manner as non-adherent cells but on the basis of whether the labels are transformed or not transformed.

23 Claims, No Drawings

(56) References Cited

OTHER PUBLICATIONS

Wang, et al., "Broadening Cell Selection Criteria with Micropallet Arrays of Adherent Cells," *Cytometry Part A.*, vol. 71(10), pp. 866-874 (2007).
International Search Report and Written Opinion for PCT/US11/61425, dated May 31, 2012, 19 pages.
Cyntellect, "LEAP™ Cell Processing Workstation." 2010. (8 pages).
Supplementary European Search Report from EP 11843656.7, dated May 14, 2014.
Sims et al.; "Choosing one from the many: selection and sorting strategies for single adherent cells"; *Anal. Bioanal. Chem.*; 387(1):5-8 (2006).
Examiner's Report from Canada Appl. No. 2818390, dated Jan. 15, 2015.

* cited by examiner

SORTING OF ADHERENT CELLS BY SELECTIVE TRANSFORMATION OF LABELS

CROSS-REFERENCE TO RELATED APPLICATIONS

This application claims the benefit of U.S. Provisional Patent Application No. 61/416,012, filed Nov. 22, 2010, the contents of which are incorporated herein by reference.

BACKGROUND OF THE INVENTION

1. Field of the Invention

This invention resides in the field of cell sorting, i.e., the selection of biological cells having particular characteristics of interest from cell populations that include both these cells and others that do not possess the characteristics of interest.

2. Description of the Prior Art

The sorting of biological cells to select cells having particular characteristics from larger populations is a procedure frequently used in biological laboratories for genomic studies, stem cell studies, and cell-based screening. Sorting allows individual cells that possess a particular characteristic to be identified and isolated for purposes of counting, further study, removal, or treatment. Sorting is commonly performed by dispersing the entire population of cells in a liquid carrier to form a suspension and then analyzing the suspension by flow cytometry to detect and either separate or individually treat the cells of interest. This method is not suitable for adherent cells, however, which are the most common phenotype of biological cells. Adherent cells can be made non-adherent, i.e., detached from the surfaces on which they are grown or from other cells to which they adhere, by enzymatic or mechanical means, but detachment is detrimental to cell health and alters the morphology of the cells and the intracellular processes that are associated with the morphology. Detachment also obliterates various traceable markers on the cell surfaces such as filopodia and localized membrane proteins which often contain the characteristics that are the reasons for the sorting.

One method for analyzing adherent cells without loss of these characteristic features is by plating the cells on a growth surface where they can be identified through a microscope. Such visual identification is tedious and prone to error, however, and robotic systems that utilize machine vision have therefore been used for greater accuracy. Whether sorting is done visually or by machine, however, complexities are involved such as the use of sacrificial base layers, the excising of sections of the surface on which the cells of interest reside, or the use of micropallets for localized plating of individual cell types.

BRIEF SUMMARY OF THE INVENTION

The method disclosed herein is one that sorts adherent cells by means that are independent of whether the cells are in the adherent state or have been released to a non-adherent state, while still sorting on the basis of any cell characteristic, including those characteristics that are present only in the adherent state. The method thus does not require the cells to be maintained in their adherent state during sorting and yet is capable of distinguishing cells with characteristics of interest observed while in their adherent state. This result is accomplished by applying a detectable and yet transformable label to the entire population of cells in their adherent state and preferentially exposing one or more subpopulations of the cells to externally applied energy that will transform the exposed labels to a state that can be differentiated from those labels that have not received the preferential exposure, with the preferential exposure performed in such a manner that the resulting difference will be retained once the entire population of cells is released from its adherent state. The subpopulation receiving the preferential exposure can either consist of the cells bearing the characteristics of interest or cells other than those bearing these characteristics. In either case, the cell characteristic on which the selection is based can be cell size, cell shape, or any other surface or intracellular feature, condition, or morphology of the cells, and yet done while the cells are still in their adherent state. Following the exposure, the cells are sorted on the basis of the difference between the exposed and unexposed labels, whether the cells are still in the adherent state or after the cells have been released from the adherent state. In embodiments of the invention in which the cells are released from the adherent state before sorting, the cell damage and cell morphology changes noted in the prior art discussion above will not prevent accurate cell sorting when the labels are applied to the cells and then selectively transformed as described herein.

DETAILED DESCRIPTION OF THE INVENTION

"Adherent cells" refers to cells, cell lines, and cell systems, whether prokaryotic or eukaryotic, that remain associated with, immobilized on, or otherwise in contact with the surface of a substrate, and remain so through washing or medium exchange procedures. Examples of cells that can be grown as adherent cells or immobilized on a surface are liver or liver-derived cells including primary hepatocytes and liver epithelial cells, epithelial cells in general, endothelial cells in general, neuronal cells, mesenchymal cells, pancreatic cells, skeletal muscle cells, cardiomyocytes, carcinoma-derived cells, bone marrow cells, islets of Langerhans, adrenal medulla cells, osteoblasts, osteoclasts, T-lymphocytes, neurons, glial cells, ganglion cells, retinal cells, and myoblast cells. Stem cells can also be used; examples are mesenchymal stem cells, neuronal stem cells, induced pluripotent stem cells, hematopoietic stem cells, mouse embryonic stem cells, and human embryonic stem cells. Many other examples exist and will be readily apparent to those of skill in the art.

Examples of transformable labels are fluorescent labels, radioactive labels, enzyme labels, nanoparticles, and microparticles, including magnetic nanoparticles and microparticles. Photolabile caged compounds, both intracellular and extracellular, can also be used. Photolabile caged compounds are precursors of active molecules that respond to irradiation with light by liberating the active molecules to a detectable form. Examples of photolabile intracellular probes are ATP, ADP, GTP, GTP-γ-S, GDP-β-S, cyclic AMP, cyclic GMP, inositol 1,4,5-triphosphate, inorganic phosphate, calcium chelators nitr-5, nitr-7, DM-nitrophen, and diazo-2. Examples of photolabile extracellular probes are carbachol, adrenaline, noradrenaline, dopamine, isoprenaline, propranolol, serotonin, glutamate, MK-801, aspartate, GABA, glycine, arachidonic acid, and nitric oxide. Nanoencapsulated labels where the capsules are light-addressable lipids can also be used. These labels include fluorophores, nanoparticles, and biomolecules, and the light addressability is the release of the labels from their lipid capsules upon exposure of the lipids to light. The fluorophores include fluorescent compounds as well as compounds that are only fluorescent when activated, such as acridone, CMNB-caged fluorescein (i.e., fluorescein bis-(5-carboxymethoxy-2-nitrobenzyl) ether), and CMNB-caged carboxyfluorescein.

The attachment of labels to cells can be achieved by means known to those of skill in the art. Attachment of a fluorescent label, for example, can be achieved by coupling members that attach either to the cell membrane or to the cell interior. Examples of coupling members are monoclonal antibodies, polyclonal antibodies, antibody fragments, non-antibody proteins, lectins, carbohydrates, short peptides, membrane-intercalating dyes, and tagged nucleic acid probes. Attachment of a radioactive label or an enzyme can be achieved by many of the same coupling members as those useful for fluorescent labels. Attachment of a nanoparticle or a microparticle can be achieved by using a carboxy-functionalized or amine-functionalized particle and coupling the particle through the carboxy or amine functional group to a ligand or an antibody by way of a carbodiimide-mediated coupling process, for example. Attachment of a lipid nanocapsule can be achieved by conventional lipid chemistry. Labels that are particles can be either fluorescent or magnetically responsive, or both. Paramagnetic particles are of particular interest in certain embodiments, and can be fabricated from such materials as polystyrene, polyethylene, and other polymers, or of metals such as magnesium, molybdenum, lithium, and tantalum.

Examples of transformable fluorescent labels are those that undergo a change in fluorescence when exposed to light energy, or to light of a particular wavelength. One such class of labels are photoactivatable fluorescent labels, including those displaying reversible photoactivation as well as those displaying irreversible photoactivation. One example of a photoactivatable fluorescent label is a photoactivatable fluorescent protein derived from the *Aequorea* genus of jellyfish which in unactivated form is non-fluorescent and upon activation emits green light. Enhanced forms of this protein, such as those containing a histidine substitution at the 203 position, have been developed and are reported in the literature, notably by Stepanenko, O. V., et al., "Fluorescent proteins as biomarkers and biosensors: throwing color lights and molecular and cellular processes," *Curr. Protein Pept. Sci.* 9: 338-369 (2008). The histidine-substituted protein, when exposed to intense illumination at 400 nm, displays a hundred-fold increase in absorption at 490 nm and a corresponding increase in fluorescence emission. Other proteins that emit red fluorescence upon exposure to light are Dendra2, IrisFP, tdEosFP, mEos2, PA-Cherryl, mKikGR, Fast-FT, Medium-FT, and Slow-FT. Still further examples are proteins known in the art as Kindling fluorescent proteins, which are activatable at 525-570 nm, and Dronpa proteins, which are activatable at 400 nm. Kindling proteins are described by Chudakov, D. M., et al., "Chromophore environment provides clue to kindling fluorescent protein riddle," *J. Biol. Chem.*, 278(9): 7215-7219 (2003), and Dronpa proteins described by Ando, R., et al., "Regulated Fast Nucleocytoplasmic Shuttling Observed by Reversible Protein Highlighting," *Science* 306(5700): 1370-1373 (2004). Examples of non-protein photoactivatable fluorescent compounds are olefins that react with singlet oxygen and hydrazides, and hydrazones that react with singlet oxygen or a peroxide with simultaneous or subsequent bond cleavage to yield fluorescent compounds. Leuco-fluorescent dyes, for example, including dihydromerocyanine dyes, are readily oxidized by singlet oxygen and thereby rendered fluorescent.

Another class of transformable fluorescent labels are photoswitchable fluorescent labels, which are labels that undergo a shift in emission wavelength upon exposure to light. Certain Kindling proteins, described in D. M. Chudakov, et al., "Photoswitchable cyan fluorescent protein for protein tracking," *Nature Biotechnol.* 22: 1435-1439 (2004), are photoswitchable. These proteins have an emission maximum that peaks at 402 nm until irradiated at 405 nm, whereupon the emission maximum shifts to 511 nm. Another example is Kaede, as described in Ando, R., et al., "An optical marker based on the UV-induced green-to-red photoconversion of a fluorescent protein," *Proc. Natl. Acad. Sci.* USA 99(20): 12651-12656 (2002). The emission maximum of Kaede shifts from 518 nm to 582 nm upon irradiation at 350-400 nm. Examples of non-protein photoswitchable fluorescent compounds are alkoxystyrobenzonitriles, a disclosed by Das, S., et al., U.S. Pat. No. 6,951,692 B1 (issue date Oct. 4, 2005). Certain dyes are classifiable as both photo-activatable and photo-switchable, depending on the wavelength.

Transformation of a fluorescent label can also be achieved by photobleaching, or the conversion of labels that are otherwise display a fluorescent response upon activation by incident light to a form that is not responsive to the same light. Photobleaching can be permanent or transitory and is readily achieved by intense or prolonged exposure of the fluorescent label to light. The light can be at the same wavelength that which is otherwise used to cause the label to fluoresce.

Transformation of a magnetic or magnetically responsive particle can be achieved by conversion of the particle to a non-magnetic or less magnetic condition, or by changing the polarization of a magnetically polarized particle in such a manner that sorting can be achieved on the basis of the polarization difference. These transformations can be achieved by exposing the particles to demagnetization energy, a prime example of which is heat. Localized heat can be generated by light energy, microwave energy, or radiofrequency energy, and other means known in the art.

The label-transforming energies cited in the preceding paragraphs and other label-transforming energies can be applied either by successive single-point exposure or by a patterned simultaneous exposure of all cites to be exposed, as explained further below Identification of the cells of interest can be performed either before or after the entire population is labeled. One means of identification, particularly when the adherent cells are arranged in a fixed two-dimensional array on the substrate to which they adhere, is to place a sample containing the adherent cells in the focal plane of a scanning and imaging system that produces a two-dimensional image of the sample and charts the two-dimensional coordinates of the cells of interest in the image. The image can for example be recorded in a charge-coupled device (CCD) and transmitted to a computer system that determines the coordinates of the cells bearing the characteristic of interest. A description of a scanning and imaging system of this type is found in Palsson et al. U.S. Pat. No. 7,505,618 B2 (issue date Mar. 17, 2009). The charted coordinates can then be used to direct energy to the cells at those coordinates or, when cells other than the cells of interest are to be transformed, the energy can be directed to locations other than those of the charted coordinates. In either case, the energy is applied in an area-patterned manner, i.e., in a two-dimensional pattern coincident with the fixed locations of the cells of interest.

Once the cells to be transformed are identified, the patterned exposure of the cells can be achieved either in a single-point successive manner (one cell at a time or one well at a time of a multi-well array where cells reside in each well) or all at once, or a combination in which segments of the area occupied by the adherent cells (or of the multi-well array) are exposed in succession, including line scans exposing successive rows or columns. Light energy is one form of energy that can be used, but other forms can also be used, depending on the label and the means by which the label is transformed. Heat energy and radiofrequency energy are examples of other forms of energy.

The single-point successive exposure can for example be achieved by a scanning laser which is programmed to direct its energy to the stored coordinates obtained in the identification step of the preceding paragraph. An example of such a procedure is likewise disclosed in the Palsson et al. patent above.

Simultaneous or semi-simultaneous exposure with light energy can be achieved by the use of a patterned energy transmission such as a spatial light modulator. A two-dimensional spatial light modulator can provide light that varies spatially in phase or amplitude, and may consist of an array of ferroelectric liquid crystal pixels, each independently addressed, using a transparent conductor such as indium tin oxide that is photolithographically patterned into individual electrodes to create independently controllable pixels. Phase modulation is achieved by light that is linearly polarized parallel to the axis of the liquid crystal material and modulated by the voltage applied across individual pixels. Amplitude modulation is achieved by rotation of the input polarization. Modulation can also be achieved in a reflective mode. Opto-electronic digital light-processing systems such as bi-stable micromirror arrays provide reflective modulation, and diffractive analogs of bi-stable systems do likewise. Micromirror systems and their operation are described in Sampsell, U.S. Pat. No. 5,610,625, issued Mar. 11, 1997 (Texas Instruments Incorporated).

Once transformation of the labels, whether those of the selected subpopulation of cells or those other than the selected subpopulation, is achieved, and thus differentiation of the cells of interest from the remaining cells, the entire population of cells can be detached from the surface or body to which they adhere, and then sorted on the basis of the transformed label in their detached state. Detachment is readily achieved by methods known in the art, prominent among which is Trypsinization, in which the cells are exposed to the protease Trypsin which cleaves the chemical bonds joining the cells to the substrate. Mechanical detachment such as by the use of a scraping tool is also effective in many cases.

Sorting through differentiation of transformed vs. untransformed labels can be achieved either with the cells in their adherent state or after release of the cells from their adherent state. For sorting after release of the cells and on the basis of fluorescence of the label, the non-adherent cells can be suspended in a carrier liquid and sorted in a flow cytometer by fluorescence-activated cell sorting (FACS) or any equivalent technique. Descriptions of fluorescence-activated cell sorting are found in Bonner, W. A., et al., "Fluorescence Activated Cell Sorting," Rev. Sci. Instr. 43(1), 404-409 (1972), and in Dittrich, W. M., et al., U.S. Pat. No. 3,761,187, issued Sep. 25, 1973. sorting on the basis of magnetism or polarization can likewise be achieved by the use of appropriate sorters, known to those of skill in the art.

In the claims appended hereto, the term "a" or "an" is intended to mean "one or more," and the "comprise" and variations thereof such as "comprises" and "comprising," when preceding the recitation of a step or an element, are intended to mean that the addition of further steps or elements is optional and not excluded. All patents, patent applications, and other published reference materials cited in this specification are hereby incorporated herein by reference in their entirety. Any discrepancy between any reference material cited herein or any prior art in general and an explicit teaching of this specification is intended to be resolved in favor of the teaching in this specification. This includes any discrepancy between an art-understood definition of a word or phrase and a definition explicitly provided in this specification of the same word or phrase.

What is claimed is:

1. A method for sorting a population of biological cells to detect a selected subpopulation thereof having a characteristic not shared by other cells of said population, said method comprising:
   (a) while cells of said population are in adherent form,
      (i) labeling cells of said subpopulation and cells not of said subpopulation with a transformable label that is capable of undergoing a transformation upon exposure to energy, the transformation resulting in a detectable difference in the label as compared with a label that has not been exposed to said energy, wherein the detectable difference is retained upon converting labeled cells from adherent form to nonadherent form,
      (ii) identifying individual cells of said population belonging to said subpopulation or not belonging to said subpopulation, and
      (iii) specifically exposing the individual cells so identified to label-transforming energy to transform labels on cells so exposed;
   (b) subsequently converting cells in adherent form of said population to nonadherent form; and
   (c) while cells of said population are in nonadherent form, sorting said population to distinguish between cells of said subpopulation and cells other than said subpopulation by differentiating between cells with labels so transformed and cells with labels that have not been so transformed.

2. The method of claim 1 wherein step (a) is performed with cells of said population arranged in a fixed two-dimensional array, and step (a) further comprises determining two-dimensional coordinates of each of said cells of said subpopulation in said array and directing said label-transforming energy either to said coordinates or to locations of said array other than said coordinates.

3. The method of claim 1 wherein said label-transforming energy is light energy.

4. The method of claim 1 wherein said label-transforming energy is heat energy.

5. The method of claim 1 wherein said label-transforming energy is radiofrequency energy.

6. The method of claim 1 wherein said labels are photoactivatable fluorescent labels, and said label-transforming energy is light energy.

7. The method of claim 1 wherein said labels are photoswitchable fluorescent labels, and said label-transforming energy is light energy.

8. The method of claim 1 wherein said labels are fluorescent labels, and said label-transforming energy is light energy sufficient to render said labels non-responsive to incident light that otherwise actuates a fluorescent emission response in said labels.

9. The method of claim 1 wherein said labels are magnetically responsive particles, and said label-transforming energy is heat energy sufficient to de-magnetize said particles.

10. The method of claim 1 wherein said labels are magnetically polarized particles, and said label-transforming energy is heat energy sufficient to produce a change of polarization in said particles.

11. The method of claim 1 wherein said labels are photolabile probes, and said label-transforming energy is light energy sufficient to render said probes detectable.

12. The method of claim 1 wherein said labels are detectable species encapsulated in lipid nanocapsules, and said label-transforming energy is light energy sufficient to rupture said lipid nanocapsules and thereby release said detectable species.

13. The method of claim 1 wherein step (a) is performed with cells of said population arranged in a fixed two-dimensional array, and said exposure of step (a) is performed by scanning said array with a source of said label-transforming energy.

14. The method of claim 13 wherein said scanning is performed by a laser.

15. The method of claim 1 wherein step (a) is performed with cells of said population arranged in a fixed two-dimensional array, and said exposure of step (a) is performed on said entire array simultaneously by two-dimensionally patterned energy transmission.

16. The method of claim 15 wherein said two-dimensionally patterned energy transmission is achieved by a spatial light modulator.

17. The method of claim 1 wherein said identifying occurs by image analysis.

18. The method of claim 1 wherein said characteristic is present only when cells of the population are in adherent form.

19. The method of claim 1 wherein said characteristic arises from markers on the cell surface.

20. The method of claim 1 wherein said characteristic is selected from the group consisting of cell size, cell shape, and cell morphology.

21. The method of claim 1 wherein step (c) is performed using fluorescence-activated cell sorting (FACS).

22. The method of claim 6 wherein the photoactivatable fluorescent labels are proteins.

23. The method of claim 22 wherein the proteins are selected from the group consisting of Dendra2, IrisFP, tdEosFP, mEos2, PA-Cherry1, mKikGR, Fast-FT, Medium-FT, Slow-FT, Kindling fluorescent proteins, and Dronpa proteins.

* * * * *